(12) United States Patent
Hunter

(10) Patent No.: US 7,530,975 B2
(45) Date of Patent: May 12, 2009

(54) MEASURING PROPERTIES OF AN ANATOMICAL BODY

(75) Inventor: Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 988 days.

(21) Appl. No.: 10/657,724

(22) Filed: Sep. 8, 2003

(65) Prior Publication Data
US 2004/0106893 A1    Jun. 3, 2004

Related U.S. Application Data

(63) Continuation of application No. 10/656,806, filed on Sep. 5, 2003, now abandoned.

(60) Provisional application No. 60/409,090, filed on Sep. 6, 2002, provisional application No. 60/424,114, filed on Nov. 5, 2002.

(51) Int. Cl.
*A61M 31/00* (2006.01)
(52) U.S. Cl. .......................... 604/500; 604/65
(58) Field of Classification Search .................. 604/65, 604/500
See application file for complete search history.

(56) References Cited

U.S. PATENT DOCUMENTS

| | | | |
|---|---|---|---|
| 2,194,535 A | 3/1940 | von Delden |
| 2,754,818 A | 7/1956 | Scherer |
| 2,928,390 A | 3/1960 | Venditty et al. |
| 3,057,349 A | 10/1962 | Ismach |
| 3,574,431 A | 4/1971 | Henderson |
| 3,659,600 A | 5/1972 | Merrill |
| 3,815,594 A | 6/1974 | Doherty |
| 3,977,402 A | 8/1976 | Pike |
| 4,108,177 A | 8/1978 | Pistor |

(Continued)

FOREIGN PATENT DOCUMENTS

EP    0 599 940 B1    12/1997

(Continued)

OTHER PUBLICATIONS

Bischoff, J.E., et al., "Finite element modeling of human skin using an isotropic, nonlinear elastic constitutive model," *Journal of Biomechanics* 33:645-652 (2000).

(Continued)

*Primary Examiner*—Nicholas D Lucchesi
*Assistant Examiner*—Victoria P Campbell
(74) *Attorney, Agent, or Firm*—Hamilton, Brook, Smith & Reynolds, P.C.

(57) ABSTRACT

A medical device includes a sensor that is configured to measure a property of an outer layer of an anatomical body surface. The sensor includes a source probe configured to stimulate a local surface of the outer layer of an anatomical body surface. The sensor also includes a detector configured to measure a response of the outer layer resulting from the source probe stimulation. A controller coupled to the source probe and the sensor drives the source probe using a tailored stochastic sequence and determines the property of the outer layer using the measured response received from the detector. The sensor can be used with medical devices, such as drug delivery devices including microneedle transport devices and needleless injection devices.

3 Claims, 15 Drawing Sheets

U.S. PATENT DOCUMENTS

| | | | |
|---|---|---|---|
| 4,206,769 A | 6/1980 | Dikstein | |
| 4,435,173 A | 3/1984 | Siposs et al. | |
| 4,447,225 A | 5/1984 | Taff et al. | |
| 4,744,841 A | 5/1988 | Thomas | |
| 4,777,599 A | 10/1988 | Dorogi et al. | |
| 4,886,499 A | 12/1989 | Cirelli et al. | |
| 5,092,901 A | 3/1992 | Hunter et al. | |
| 5,116,313 A | 5/1992 | McGregor | |
| 5,242,408 A * | 9/1993 | Jhuboo et al. | 604/152 |
| 5,244,461 A * | 9/1993 | Derlien | 604/65 |
| 5,318,522 A | 6/1994 | D'Antonio | |
| 5,347,186 A | 9/1994 | Konotchick | |
| 5,354,273 A | 10/1994 | Hagen | |
| 5,405,614 A | 4/1995 | D'Angelo et al. | |
| 5,478,328 A | 12/1995 | Silverman et al. | |
| 5,480,381 A | 1/1996 | Weston | |
| 5,505,697 A | 4/1996 | McKinnon, Jr. et al. | |
| 5,622,482 A | 4/1997 | Lee | |
| 5,694,920 A | 12/1997 | Abrams et al. | |
| 5,722,953 A | 3/1998 | Schiff et al. | |
| 5,840,062 A | 11/1998 | Gumaste et al. | |
| 5,919,167 A | 7/1999 | Mulhauser et al. | |
| 6,004,287 A | 12/1999 | Loomis et al. | |
| 6,030,399 A | 2/2000 | Ignotz et al. | |
| 6,037,682 A | 3/2000 | Shoop et al. | |
| 6,048,337 A | 4/2000 | Svedman | |
| 6,056,716 A | 5/2000 | D'Antonio et al. | |
| 6,074,360 A | 6/2000 | Haar et al. | |
| 6,123,684 A | 9/2000 | Deboer et al. | |
| 6,132,385 A * | 10/2000 | Vain | 600/553 |
| 6,203,521 B1 | 3/2001 | Menne et al. | |
| 6,258,062 B1 | 7/2001 | Thielen et al. | |
| 6,272,857 B1 | 8/2001 | Varma | |
| 6,375,624 B1 | 4/2002 | Uber, III et al. | |
| 6,375,638 B2 | 4/2002 | Nason et al. | |
| 6,408,204 B1 | 6/2002 | Hirschman | |
| 6,565,532 B1 | 5/2003 | Yuzhakov et al. | |
| 6,611,707 B1 | 8/2003 | Prausnitz et al. | |
| 6,626,871 B1 | 9/2003 | Smoliarov | |
| 6,656,159 B2 | 12/2003 | Flaherty | |
| 6,678,556 B1 | 1/2004 | Nolan et al. | |
| 6,723,072 B2 | 4/2004 | Flaherty et al. | |
| 6,743,211 B1 | 6/2004 | Prausnitz et al. | |
| 6,770,054 B1 | 8/2004 | Smolyarov et al. | |
| 2002/0145364 A1 | 10/2002 | Gaide et al. | |
| 2005/0022806 A1 | 2/2005 | Beaumont et al. | |

FOREIGN PATENT DOCUMENTS

| | | |
|---|---|---|
| EP | 0 834 330 A2 | 4/1998 |
| EP | 1 020 200 A2 | 7/2000 |
| EP | 0 710 130 B1 | 12/2000 |
| GB | 686343 | 1/1953 |
| JP | 06327639 | 11/1994 |
| JP | 01046344 | 2/2001 |
| WO | WO 00/23132 | 4/2000 |
| WO | WO 01/26716 A1 | 4/2001 |
| WO | WO 01/37907 A1 | 5/2001 |
| WO | WO 02/100469 A2 | 12/2002 |

OTHER PUBLICATIONS

Diridollou, S., "Sex- and site-dependent variations in the thickness and mechanical properies of human skin in vivo," *International Journal of Cosmetic Science* 22:421-435 (2000).

Flynn, D.M., et al., "A Finite Element Based Method to Determine the Properties of Planar Soft Tissue," *Journal of Biomechanical Engineering* 120(2):202-210 (1998).

He, M.M., et al., "Two-Exponential Rheological Models of the Mechanical Properties of the Stratum Corneum," *Pharmaceutical Research* 13:S1-S604 (1996).

Hirota, F.G., et al., "An Implicit Finite Element Method for Elastic Solids in Contact," *IEEE*:136-146 (2001).

Korenberg, M.J. and Hunter, I.W., "The Identification of Nonlinear Biological Systems: Volterra Kernel Approaches," *Annals of Biomedical Engineering*, 24:250-268 (1996).

Lindahl, O.A., et al., "A tactile sensor for detection of physical properties of human skin in vivo," *Journal of Medical Engineering & Technology*, 22(4):147-153 (1998).

Manschot, J.F.M. and Brakkee, A.J.M., "The Measurement and Modelling of the Mechanical Properties of Human Skin In Vivo-I. The Measurement," *J. Biochem.* 19(7):511-515 (1986).

Manschot, J.F.M. and Brakkee, A.J.M., "The Measurement and Modelling of the Mechanical Properties of Human Skin In Vivo-II. The Model," *J. Biomechanics* 19(7):517-521 (1986).

Menciassi, A., et al., "An Instrumented Probe for Mechanical Characterization of Soft Tissues," *Biomedical Microdevices* 3(2):149-156 (2001).

Oka, H. and Irie, T., "Mechanical impedance of layered tissue," *Medical Progress through Technology, Supplement to* vol. 21:1-4 (1997).

Patton, R.L., "Mechanical Compliance Transfer Function Analysis for Early Detection of Pressure Ulcers." Unpublished master's thesis, Massachusetts Institute of Technology, Cambridge, MA. (1999).

Reihsner, R., et al., "Two-dimensional elastic properties of human skin in terms of an incremental model at the in vivo configuration," *Med. Eng. Phys.* 17(4):304-313 (1995).

Soong, T.T. and Huang, W.N., "A Stochastic Model for Biological Tissue Elasticity," Proceedings of the Fourth Canadian Congress of Applied Mechanics, Montreal, Canada (1973).

Zhang, M. and Roberts, V.C., "The effect of shear forces externally applied to skin surface on underlying tissues," *J. Biomed. Eng.* 15:451-456 (1993).

Goussard, Y. et al., "Practical Identification of Functional Expansions of Nonlinear Systems Submitted to Non-Gaussian Inputs," *Annals of Biomedical Engineering*, 19: 401-427 (1991).

Lee, Y.W. and Schetzen, M., "Measurement of the Wiener Kernels of a Non-linear System by Cross-correlation," *International Journal of Control*, II(3): 237-254 (1965).

* cited by examiner

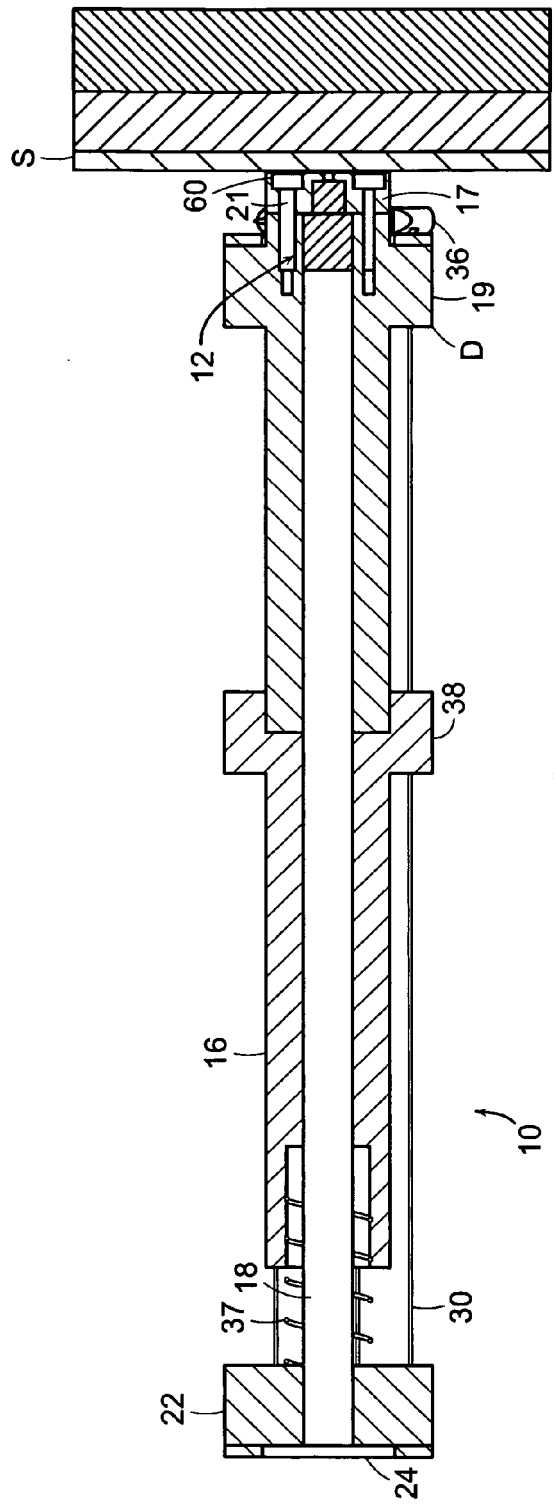
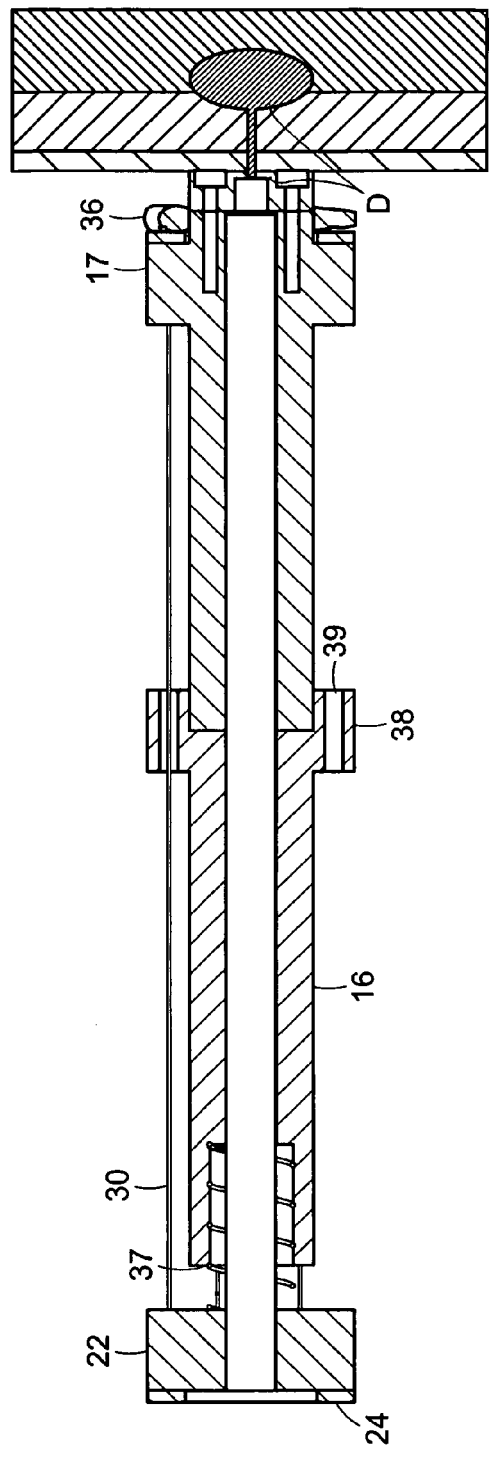
FIG. 5A
FIG. 5B

MEASURING PROPERTIES OF AN ANATOMICAL BODY

RELATED APPLICATIONS

This application is a Continuation of U.S. application Ser. No. 10/656,806 filed on Sep. 5, 2003 now abandoned which claims the benefit of U.S. Provisional Application Nos. 60/409,090, filed Sep. 6, 2002 and 60/424,114, filed Nov. 5, 2002. The entire teachings of the above applications are incorporated herein by reference.

BACKGROUND

Injection of a liquid such as a drug into a human patient or an agriculture animal is performed in a number of ways. One of the easiest methods for drug delivery is through the skin which is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10-20 microns from the skin surface and has no blood supply. Because of the density of this layer of cells, moving compounds across the skin, either into or out of the body, can be difficult.

The current technology for delivering local pharmaceuticals through the skin includes methods that use needles or other skin piercing devices. Invasive procedures, such as use of needles or lances, effectively overcome the barrier function of the stratum corneum. However, these methods suffer from several major disadvantages: local skin damage, bleeding, and risk of infection at the injection site, and creation of contaminated needles or lances that must be disposed. Further, when these devices are used to inject drugs in agriculture animals, the needles break off from time to time and remain embedded in the animal.

Needleless injection devices have been proposed to overcome the problems associated with needles, but the proposed devices present different problems. For example, some needleless injection devices rely on spring actuators that offer limited control. Others use solenoids, compressed air or hydraulic actuators also offer limited control.

SUMMARY

Skin sensor apparatus and methods described herein use specially tailored stimulation to effectively measure one or more properties of the surface of an anatomical body, such as the compliance gain and/or stiffness of skin.

A medical device includes a sensor configured to measure a property of an outer layer of an anatomical body surface. The sensor includes a source probe configured stimulate a local surface of the outer layer of an anatomical body surface. The sensor also includes a detector configured to measure a response of the outer layer resulting from the source probe stimulation. Further, the device includes a controller coupled to the sensor. The controller drives the source probe using a tailored stochastic sequence. The controller then determines the property of the outer layer using the measured response received from the detector.

The body surface can be the skin of a subject, or an internal body surface. The body surface can be modeled as a second order mechanical system. Further, the property of the outer layer can be determined using system identification techniques.

The source probe can include a voice coil for stimulating the local surface of the outer layer. For example, the voice coil can be coupled to the outer layer and driven at a frequency to displace the surface. The detector measures displacement of the body surface, for example, using an accelerometer. In one embodiment, the detector includes a linear differential variable transducer detecting displacement of the body surface. In some embodiments, the detector further includes a strain gauge for measuring a static displacement of the body surface.

The medical device can be a drug injection device. The drug injection device is coupled to the sensor and injects a drug into an anatomical body in response to the determined property of the outer layer. For example, the device can include a servo-controller coupled to a delivery device for delivering a pharmaceutical. The servo-controller adjusts the delivery characteristics of the delivery device based on the surface properties. In one embodiment, the drug injection device is a needleless injector.

A device for injecting drug into a biological body includes a drug injector for holding the drug to be delivered to the body. The device also includes a skin sensor that measures skin properties of the body and a servo-controller coupled to the drug injector and the skin sensor. The servo-controller adjusts the injection pressure of the drug injector to selectively deliver the drug to the body based on the skin properties. In some embodiments, the skin sensor measures the properties of the body using a tailored stochastic sequence.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5A is a cross-sectional view of the drug delivery device taken along the line 5A-5A of FIG. 1C prior to delivery of a drug.

FIG. 5B is a cross-sectional view of the drug delivery device of FIG. 1A during drug delivery.

DETAILED DESCRIPTION OF THE INVENTION

A description of preferred embodiments of the invention follows.

Figure 1:
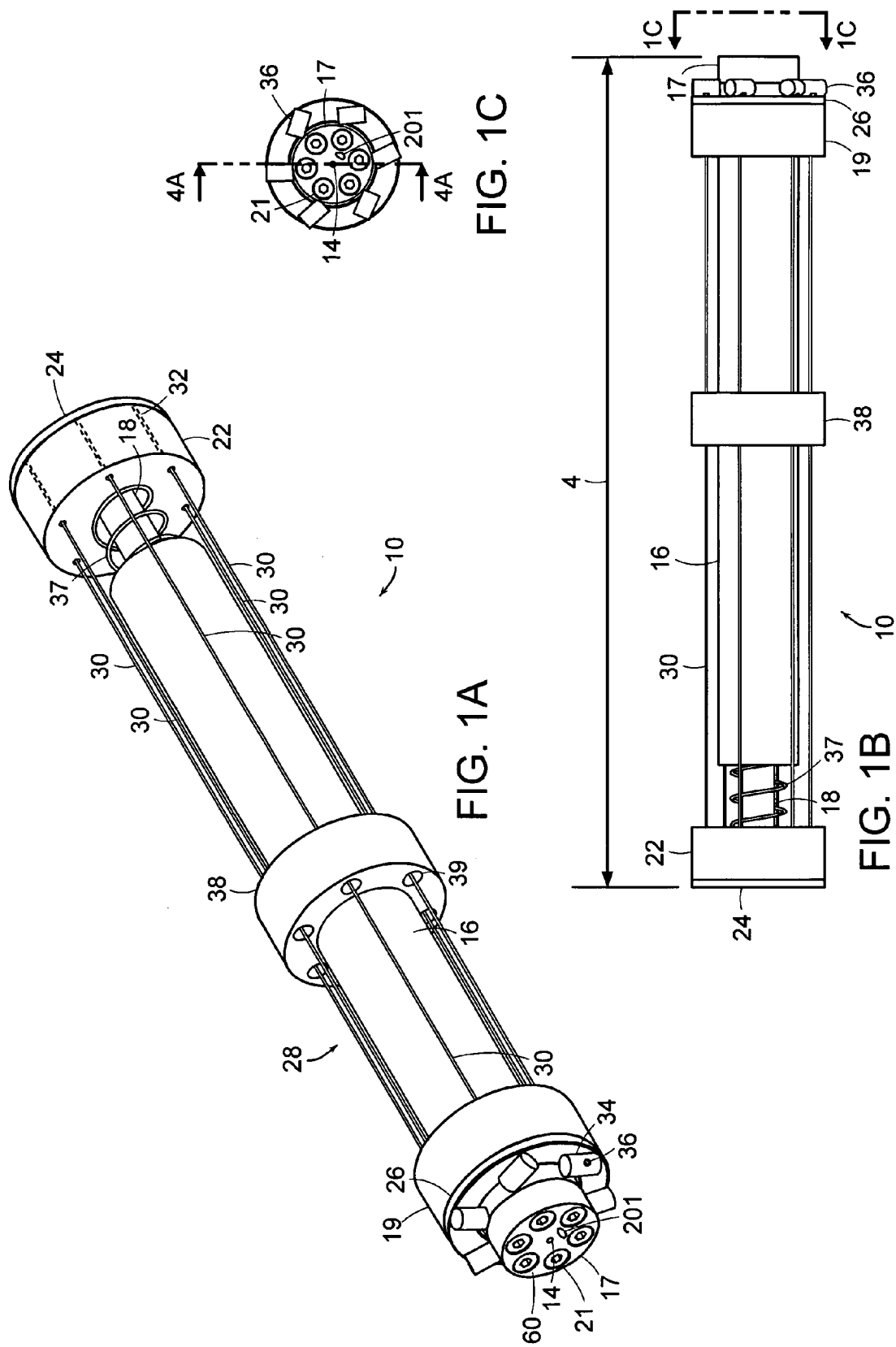
FIG. 1A is a perspective view of a drug delivery device in accordance with the invention.
FIG. 1B is a side view of the drug delivery device of FIG. 1A.
FIG. 1C is an end view of the drug delivery device taken along the line 1C-1C of FIG. 1B.

Referring to FIGS. 1A-1C, there are shown various views of a drug delivery device used to inject a liquid formulation of an active principle, for example, a drug, into biological body such as an agriculture animal or human being. The delivery device is generally identified as 10 in the illustrated embodiment as well as in other embodiments described later. The drug is initially contained in a chamber 12 (FIG. 5A) and is injected out through an orifice or output port 14 into the body.

A nozzle is typically used to convey the drug to the skin at the required speed and diameter to penetrate the skin as required. The nozzle generally contains a flat surface, such as the head 17 that can be placed against the skin and an orifice 14. It is the inner diameter of the orifice 14 that controls the diameter of the drug stream. Additionally, the length of an aperture, or tube, defining the orifice 14 also controls the injection pressure. In some embodiments, a standard hypodermic needle is cut to a predetermined length and coupled to the head. One end of the needle is flush, or slightly recessed, with respect to the surface of the head 17 that contacts the skin to avoid puncturing the skin during use. The internal diameter of the needle (e.g., 100 μm) defines the diameter of the aperture, and the length of the needle (e.g., 5 mm) together with the aperture dimension controls the resulting injection pressure, for a given applicator pressure. In other embodiments, a hole can be drilled directly into the head 17 to reduce assembly steps. In general, the length of the orifice is selectable, for example ranging from 500 μm to 5 mm, while its diameter can range from 80 μm to 200 μm.

The device 10 includes a guide tube 16 in which a piston 18 is positioned. An interchangeable head 17 is attached at an enlarged end 19 of the tube 16 with a set of screws 21. One end of the piston 18, along with the inside of the enlarged end 19 and head 17 define the chamber 12, and a push block 22 is attached at the other end of the piston 18. Although the piston 18 forms a clearance seal with the tube 16, a seal ring can be placed about the piston 18 to prevent drug from escaping from the chamber 12 between the piston 18 and the tube 16. Attached on the outside of the push block 22 is an electrical contact plate 24. Another contact plate 26 is positioned between the interchangeable head 17 and the enlarged end 19.

In some embodiments, the guide tube 16 includes linear bearings to reduce the friction of the piston 18. Preferably, the piston 18 is rigid to avoid buckling under the force exerted by the actuator. Further, the piston 18 is light weight to reduce its inertia ensuring a rapid acceleration upon activation. In one embodiment, the piston 18 is formed from a hollow aluminum rod. Other parts can also be advantageously constructed of light weight materials. For example, the push block 22 can be formed from a machinable poly acetal.

In addition to the contact plates 24 and 26, an actuator 28 includes one to six or more wires 30 positioned about the tube 16 and parallel to one another. One end 32 of each wire 30 is attached to the contact plate 24 through the push block 22, and another end 34 of the wire 30 is attached to a respective capstan 36. The capstan 36, and the contact plates 24 and 26 are electrically conductive. Hence, the ends 32 and 34 of the wires 30 are electrically connected to each other through the contact plates 24 and 26, respectively. An insulating collar 38 positioned about the guide tube 20 helps guide the wires 30 through the holes 39 between the enlarged region 19 and the push block 22.

To apply the appropriate tension to the wires 30 and to define the volume of the chamber 12, a coiled spring 37 is positioned about the piston 18 between the end of the tube 16 and the push block 22, and the capstans 36 are turned accordingly, much like adjusting the tension in guitar strings. The wires 30 are wrapped around the respective capstans 36 one or more times. As such, the strain near the terminal ends 34 of the wires 30 attached to the capstans 36 are significantly less than the strain along the remainder of the length of the wires 30. For example, the strain near the terminal end 34 may be about 1% while that of the remainder of the wire may be about 15%.

The wires 30 can be secured to the contact plate 24 with capstans, as well. Alternatively, the wires 30 can be attached to one or both contact plates 24 and 26 by other techniques, for example, by electrodeposition as described in U.S. Pat. No. 5,641,391, the entire contents of which are incorporated herein by reference.

Alternatively, each wire 30 can be twisted with a respective electrically conductive wire made of, for example, copper or iron. The twisted segment is then bent back, and partially twisted forming a loop, with the partially twisted segment formed of two strands of the wire 30 and two strands of the copper wire. The formed loop can be placed on a pin, for example, or it can be fully twisted and then bent back and partially twisted forming another loop, with the partially twisted segment formed of four strands of the wire 30 and four strands of the copper wire. Again, the formed loop can be placed on a pin to secure the wire 30 to the contact plate 24 and/or 26.

More generally, the wires 30 can be formed from a shape memory material that changes from a first stable state to a second stable state upon excitation. For example, the shape memory material can be a shape memory polymer. Alternatively, or in addition, the shape memory material can be an alloy. In some embodiments, a phase change of the shape memory material occurs when the material is heated. For example, a shape metal alloy can exist with one of two different lattice structures, such that a phase change from one lattice structure to another occurs responsive to the application and/or removal of thermal energy.

The wires 30 are made of a suitable material that contracts when heated and can be used as an actuation method. Heating can be accomplished by passing a current through the wire 30, known as Joule heating. Thus, the current is conducted within the wires 30 after a potential is applied across them. A class of materials that contract when a potential is applied to them includes piezoelectric materials and shape memory alloys. While piezoelectric crystals contract about 1%, shape memory alloys are able to contract approximately 15% or more. The larger contraction of shape memory alloys makes them desirable for the illustrated embodiment. Accordingly, the wires 30 are made of shape memory alloy such as, for example, Ni—Ti (also known as Nitinol), available from Shaped Memory Applications Inc., of San Jose, Calif., and from Dynalloy Inc. of Costa Mesa, Calif., under the Trade Mark FLEXINOL. When a potential is applied across the wires 30 via the contact plates 24 and 26 the wires 30 heat up. As the wires 30 heat up, a phase transformation of the wire material occurs, namely, the wire changes phase from martensite to austenite. This phase transformation causes the wires 30 to contract such that the piston 18 is pushed towards the orifice 14, thereby forcing the drug from the chamber 12 out the orifice 14. Preferably, the shape memory alloy is fast acting to provide a sudden force suitable for injecting a drug into a patient's skin without using a needle. A more detailed description of shape memory alloys and their use is described in U.S. Pat. No. 5,092,901, the entire contents of which are incorporated herein by reference.

Figure 2:
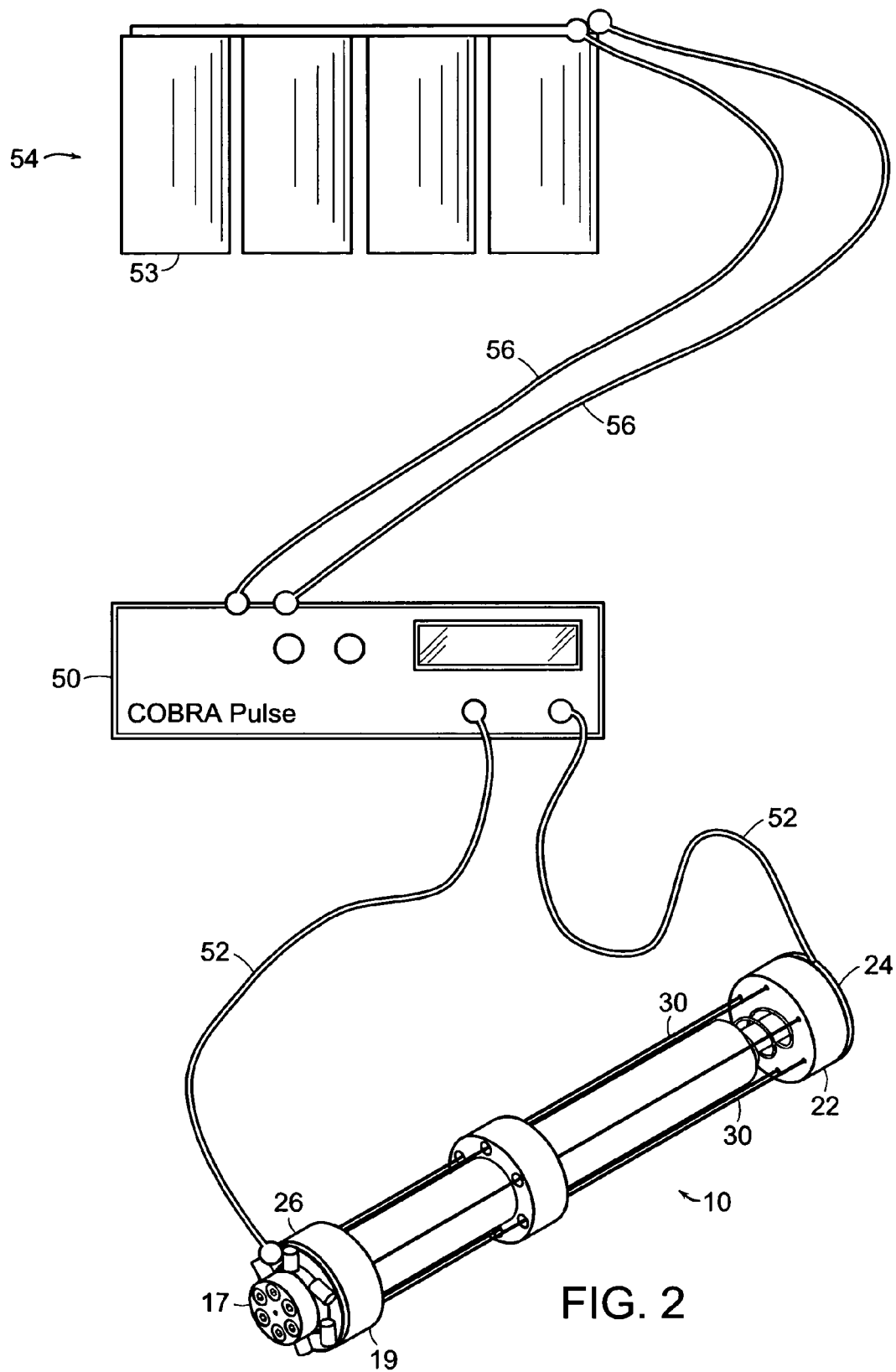
FIG. 2 is a perspective view of the drug delivery device of FIG. 1A with a controller and energy source.

To use the device 10, the device is connected to a controller 50 with a pair of leads 52, and the controller in turn in connected to a capacitor bank 54 with another pair of leads 56, as illustrated in FIG. 2. The controller 50 can be a simple microprocessor, or alternatively a personal computer with multifunction capabilities. The capacitors of the bank 54 are energized through a power source in the controller 50 or by an external power source. Once energized, the capacitors, under the direction of the controller 50, discharge to apply a potential across the wires 30 via the plates 24 and 26 through the leads 52. In this manner, the wires 30 are connected together in a parallel configuration, the supply potential being applied equally across the ends of each of the multiple wires 30. In another embodiment, the wires 30 are connected together in a series configuration. Still other arrangements can be used to apply the potential across the wires 30, for example, as describe in U.S. application Ser. No. 10/200,574 filed Jul. 19, 2002, by Angel and Hunter, the entire contents of which are incorporated herein by reference.

Although any capacitor can be used in the bank 54, a super capacitor has the advantageous feature of providing a large energy density in a small physical size. Hence the capacitors of the bank 54 can be super capacitors 53 that have a volume from 1.5 ml to 30 ml, preferably 3 ml, and an energy output of 10 J to 1 KJ, preferably 100 J. The current applied to the wires 30 is approximately 100 mAmps to 5 Amps, and the voltage applied to the wires 30 is between about 1 volt to 10 volts. In one embodiment, the applied current is 1 Amp, and the applied voltage is 5 volts. To heat the wires 30 quickly, larger currents of 25 to 100 Amps can be applied. As fast action is required, the power source must also be able to switch large currents with millisecond timing.

The amount of force per area generated by the wires 30 is about 235 $MN/m^2$. In the illustrated embodiment, the volume of drug initially contained in the chamber 12 is about 200 μL to 250 μL, and the orifice 14 has a diameter of between about 50 μm to 500 μm. In some embodiments, the drug volume is up to 500 μL. The drug injection velocity is about 150 m/s with a 150 μm orifice 14. Generally, an injection velocity of 100 m/s or greater is required for successful skin penetration (e.g., penetrating skin to a depth of 2 mm) in a stream having a diameter of 100 μm. Advantageously, the stream diameter of the needleless injector can be substantially smaller than a typical 24 gauge needle having a diameter of 450 μm.

The device 10 has a length, $L_1$, of approximately 150 mm, and the wires 30 contract about 7 mm when a potential is applied across them. The wires 30 can have circular cross section, in which case each wire 30 has a diameter of approximately 0.025 mm to 2 mm, preferably 380 μm. Alternatively, each fiber can have a flat ribbon shape with a thickness approximately in the range 0.025 mm to 0.5 mm and a width of approximately 0.75 mm to 10 mm. Other suitable shape memory alloys include Ag—Cd, Au—Cd, Au—Cu—Zn, Cu—Al, Cu—Al—N, Cu—Zn, Cu—Zn—Al, Cu—Zn—Ga, Cu—Zn—Si, Cu—Zn—Sn, Fe—Pt, Fe—Ni, In—Cd, In—Ti, and Ti—Nb.

Figure 3A:
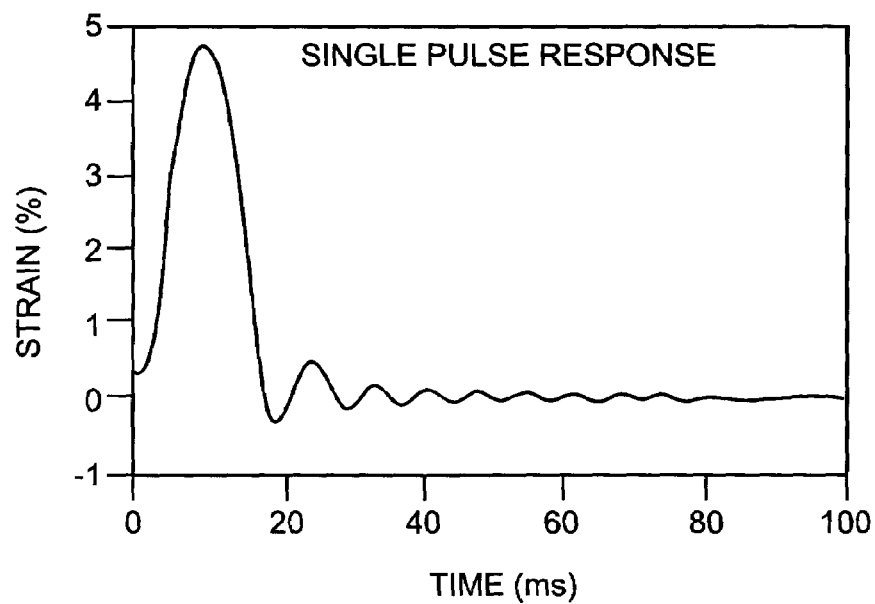
FIG. 3A is a graph of the time response of a shape memory alloy fiber of the drug delivery device of FIG. 1A for a high strain.
Figure 3B:
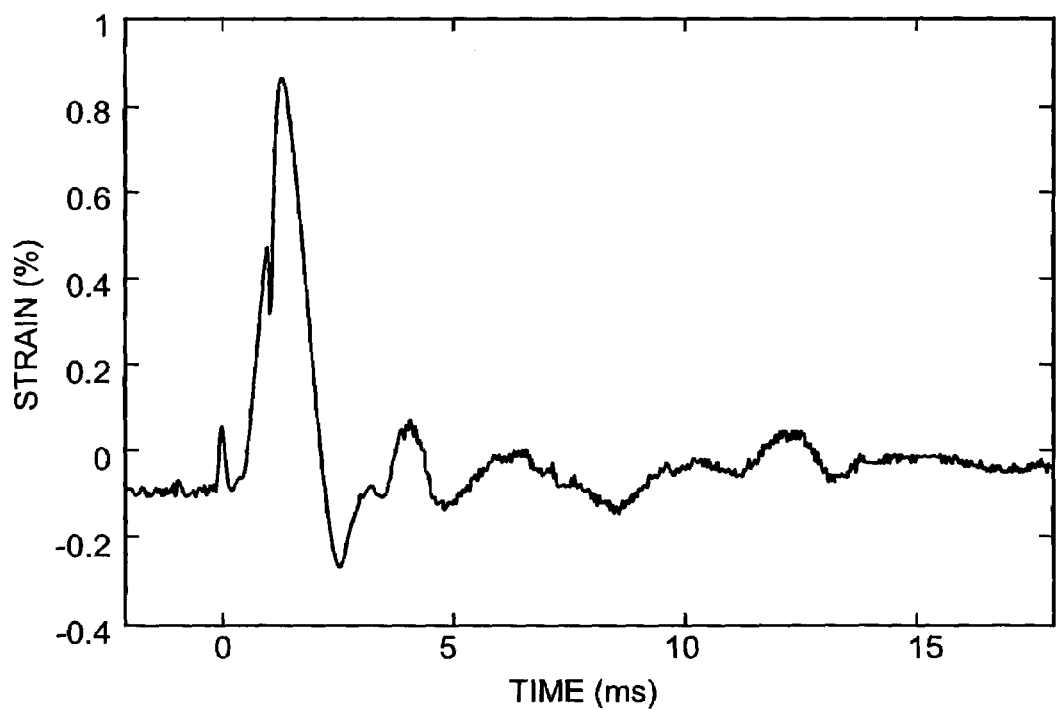
FIG. 3B is a graph of the time response of the shape memory alloy fiber of the drug delivery device of FIG. 1A when the fiber is subjected to a potential as a quick pulse.

Referring now to FIGS. 3A and 3B, there are shown graphs of the time response of wires 30 made from Ni—Ti. Shown in FIG. 3A is the response of a wire subjected to a strain of nearly 5%. As can be seen, the contraction time for this wire is about 10 ms. By way of contrast, FIG. 3B illustrates a wire subjected to faster pulse than that applied to the wire of FIG. 3A. With the faster pulse, the fiber experiences a strain of about 1%, with a contraction time of about 1 ms.

Figure 4D:
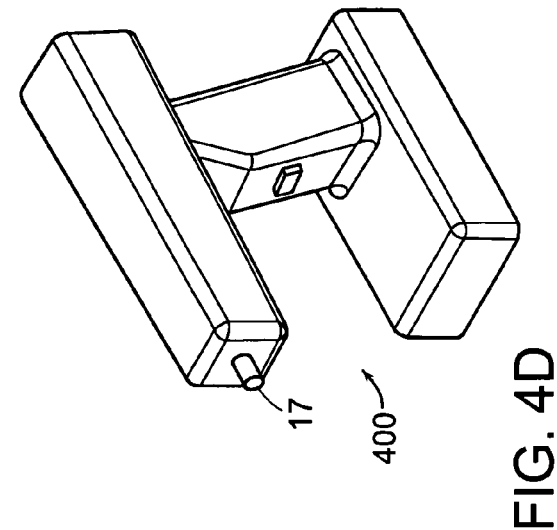
FIG. 4D is a perspective view of the drug delivery device shown in FIGS. 4A-4C.
Figure 4A:
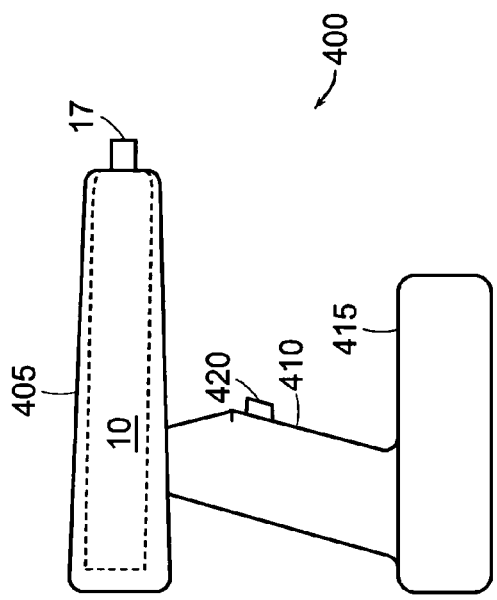
FIGS. 4A-4C are respectively side, front, and top views of a hand-held drug delivery device.
Figure 4B:
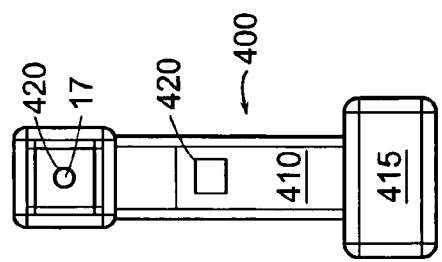
Figure 4C:
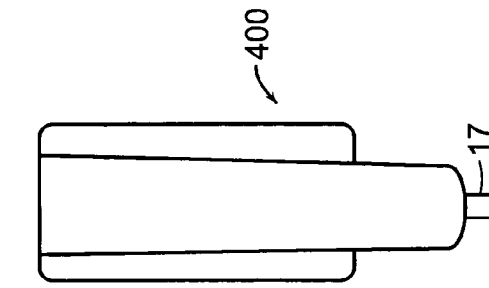

In use, the device 10 is typically mounted within an applicator that is held by an operator. The applicator can be shaped as a pistol, cylinder or any other suitable geometry. An exemplary applicator is shown in FIGS. 4A through 4D. In one embodiment, referring to FIG. 4A, a pistol shaped applicator 400 includes a barrel 405 configured to house the device 10. The barrel 405 can be a hollow tube or rectangle having a cavity sized to accept the device 10. Referring to FIG. 4B, the barrel 405 includes an aperture 420 at one end sized to accept the head 17 of the device 10. The head 17 protrudes through the aperture 420 to facilitate contact with an animal's skin. Further, the applicator 400 includes a handle 410 configured to be grasped by an operator. The handle 410 is coupled at one end to the barrel 405. Additionally, the applicator 400 can include a base 415 coupled to another end of the handle 410. The base 415 can be configured to house other parts of the needleless injector, such as the power source and/or control unit. The handle 410 can be similarly configured (e.g., hollowed out) to also house parts of the needleless injector. Further, the applicator 400 can include a switch 420. The switch 420 can be controlled by an operator to operate the device 10 to initiate an injection and/or a filling of the device with a drug.

Referring to FIGS. 5A and 5B, as well as to FIG. 1A, the operator positions the applicator to place a surface 60 of the head 17 against the skin, S, of the biological body. Prior to the placement of the head 17 against the skin, or while the head 17 is positioned against the skin, the capacitor bank 54 is energized as described above. The operator then triggers the device 10 through the controller 50 to discharge the capacitor bank 54, thereby applying a potential across the wires 30 which causes them to contract. As the wires 30 contract, they pull the push block 22, which pushes the piston 18 towards the head 17 to force the drug, D, from the chamber 12 through the orifice 14 into the body. The injection pressure can be as low as 1 MPa or lower or as high as 300 MPa. For comparison, a minimum local pressure of approximately 1.91 MPa is required for piercing skin to a depth of 2 mm using a 100 μm diameter needle After the energy in the capacitor bank is depleted, the potential across the wires 30 is removed which causes the wires 30 to extend to their original length as the coiled spring 37 pushes the push block 22 away from the head 17. The chamber 12 can then be refilled if desired with additional drug to be injected into another body or the same body.

Turning now to FIGS. 6A-6D, there are shown various views of an alternative embodiment of the drug delivery device 10, where like features are identified by like numerals. Here, the device 10 includes two base portions 70 and 72. The piston 18 extends through the base portion 72 and through part of the base portion 70, as shown, for example, in FIG. 9A. As before, the piston 18 is attached at one end to the push block 22, which slides back and forth over a surface 76 of the base portion 72, such that the piston slides back and forth in the base portions.

Figure 7A:
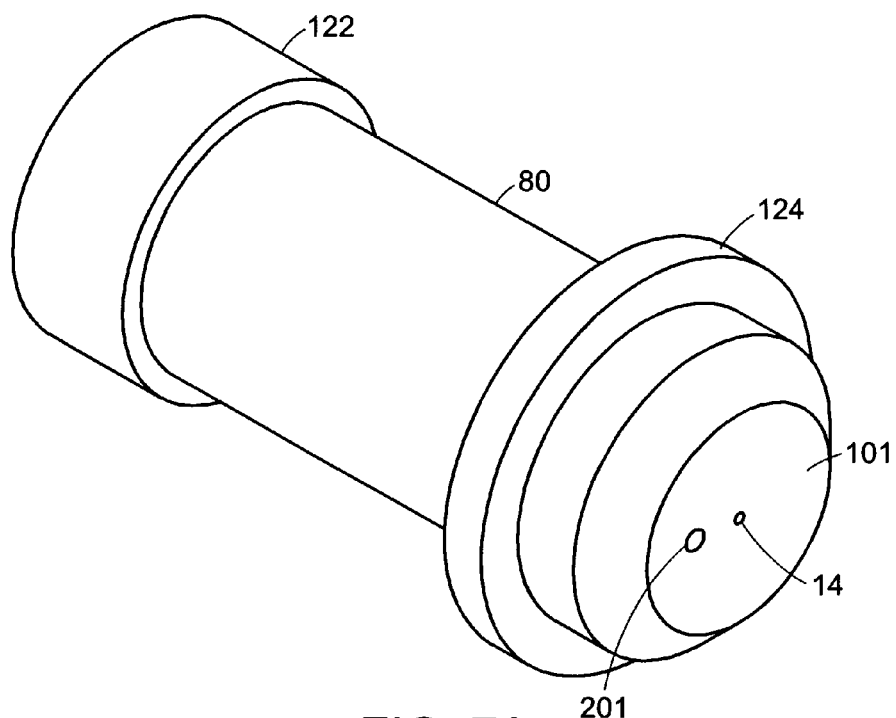
FIG. 7A is a perspective view of a drug vile for the drug delivery device of FIG. 6A.
Figure 7B:
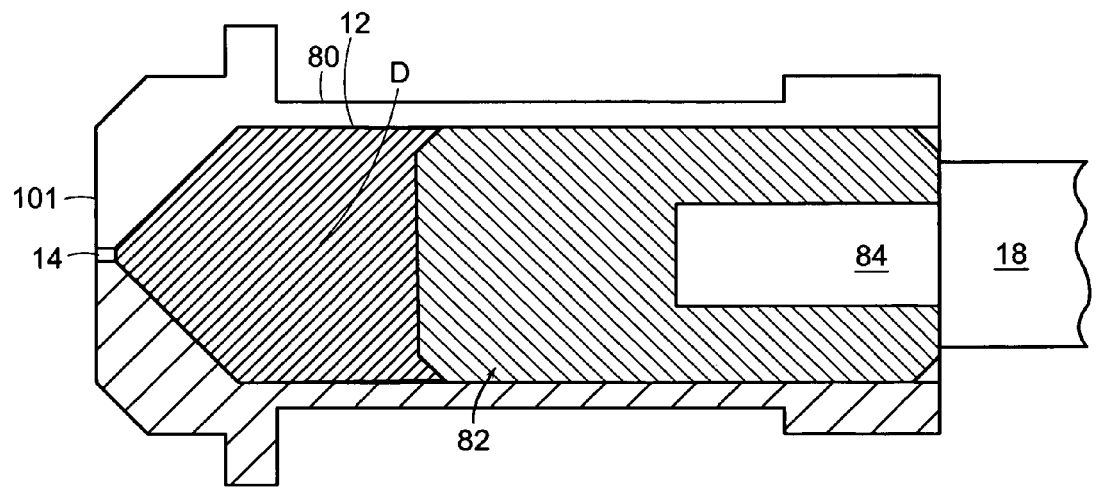
FIG. 7B is a cross-sectional view of the drug vile of FIG. 7A.

Referring also to FIGS. 7A and 7B, a removable and/or disposable vial 80 is mounted in the base portion 70. For example, the vial 80 can be screw mounted to the base portion 70. The vial 80 is provided with a nozzle, as described above, at one end defining the orifice 14. The vial 80 also includes a plunger 82 that moves back and forth in the chamber 12 defined within the vial 80. The plunger 82 abuts the terminal end 84 of the piston 18. As such, as the piston 18 moves towards the orifice 14, drug, D, contained in the chamber 12 is expelled through the orifice 14. In some implementations, the orifice of the drug vial, or the chamber of the embodiment of FIG. 1A, is sealed with a suitable material prior to use. The seal may be manually removed, or it may be removed by the injection pressure of the drug as it ejects from the vial or chamber.

A single length wire 30 is positioned on each side of the base portions 70 and 72 and attached at one end to a lead capstan 90a, wrapped sequentially around intermediate capstans 90b, 90c, 90d, and attached at the other end to a terminal capstan 90e. To apply the appropriate tension to the wires 30, the coiled spring 37 is positioned about the piston 18 between the base portion 72 and the push block 22, and a rachet mechanism 92 is employed to adjust the tension in the wires 30. The capstans 90a, 90c, and 90e are electrically conductive, and are coupled to respective conductive bars 94 and 96. The capstans 90b and 90d are also electrically conductive, and are electrically coupled to respective conductive plates 98 and 100. The plates 98 and 100 in turn are electrically connected to each other through the push block 22, but electrically insulated from the piston 18 and base portion 72. The two bars 94 and 96 are electrically insulated from the base portion 70. As such, when a potential is applied across the conductive bars 94 and 96, the potential is also applied across the four segments of each wire 30.

Figure 6A:
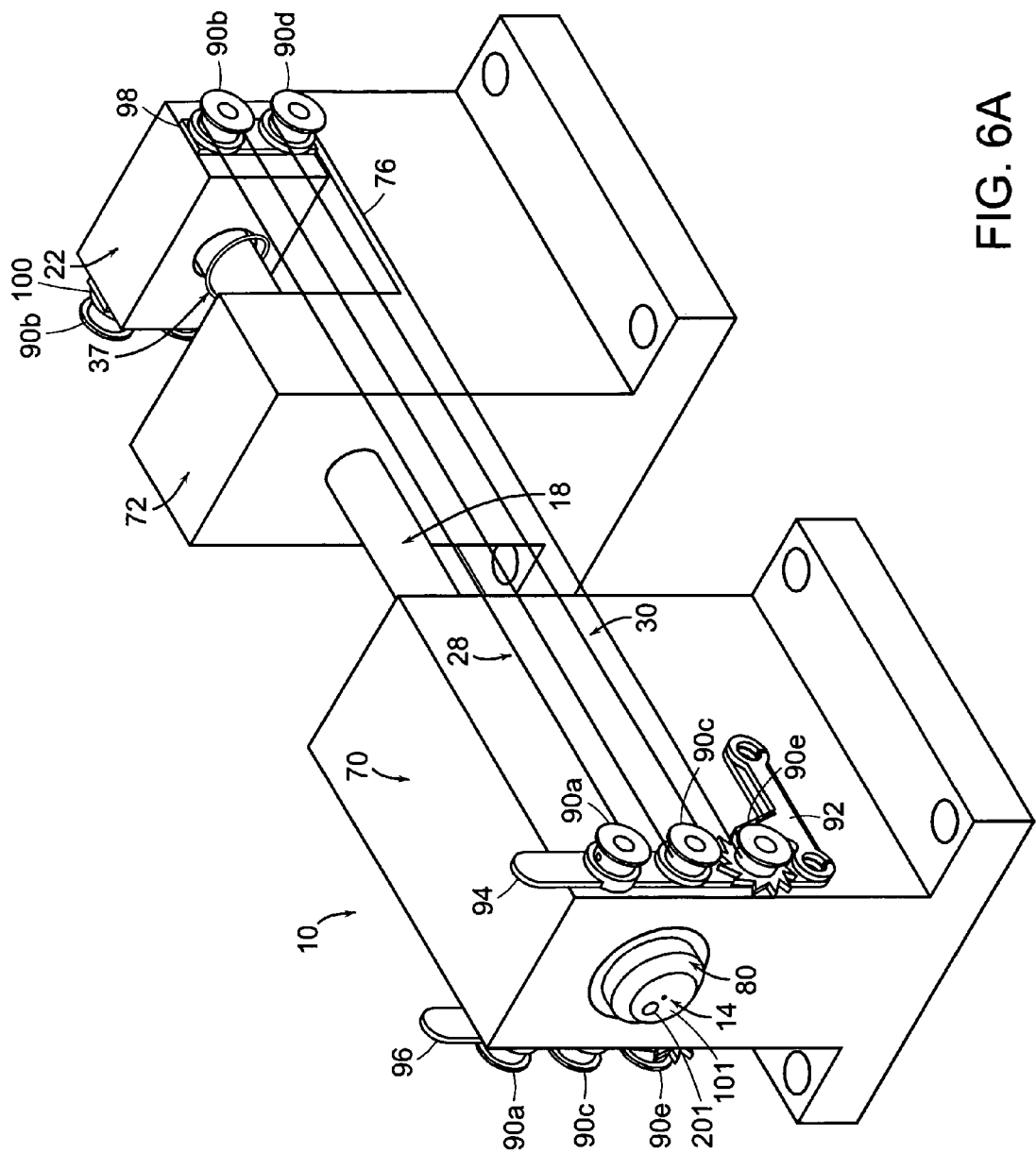
FIG. 6A is a perspective view of an alternative embodiment of the drug delivery device in accordance with the invention.
Figure 6B:
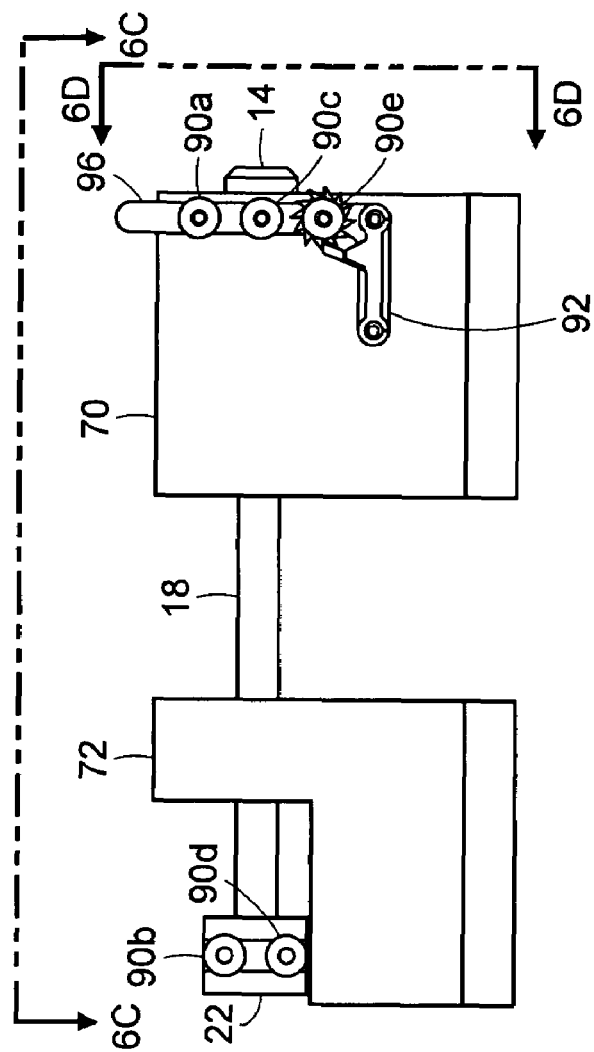
FIG. 6B is a side view of the drug delivery device of FIG. 6A.
Figure 6D:
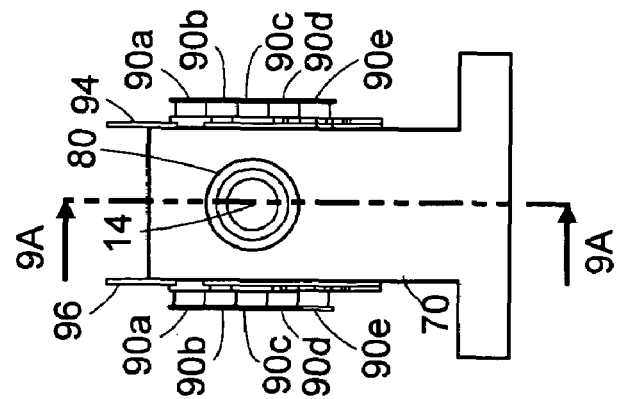
FIG. 6D is front view of the drug delivery device taken along the line 5D-5D of FIG. 6B.
Figure 6C:
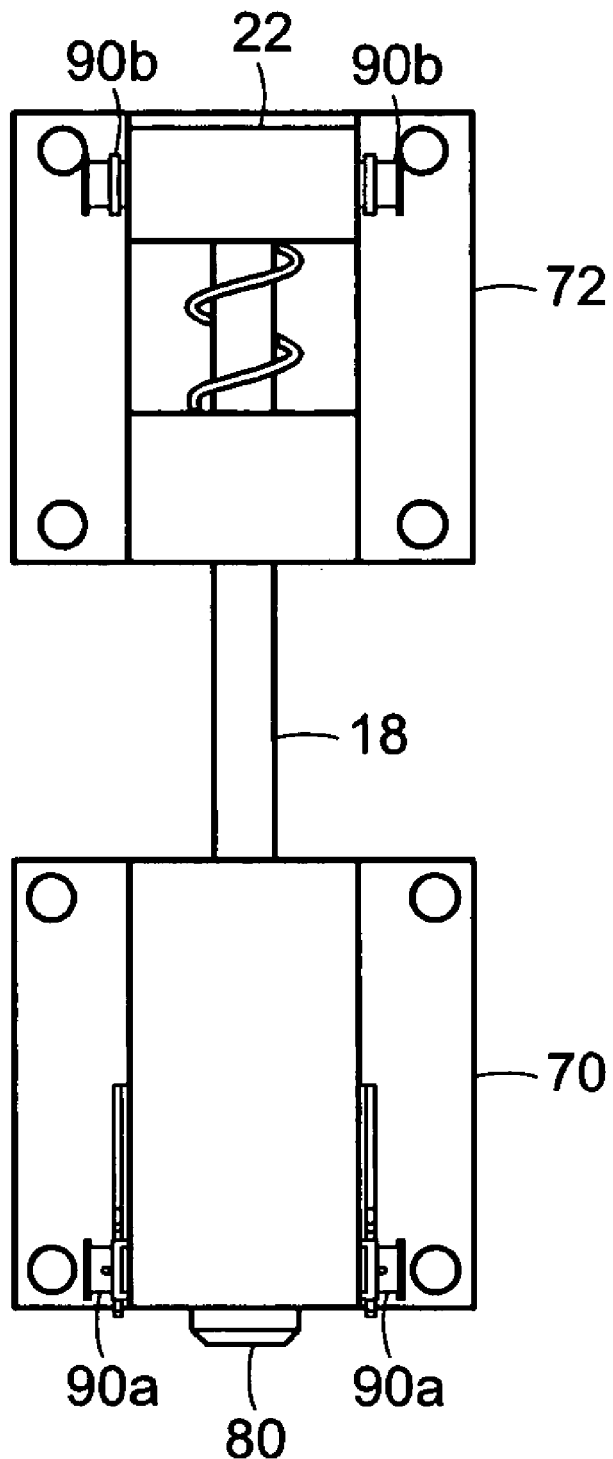
FIG. 6C is top view of the drug delivery device taken along the line 6C-6C of FIG. 6B.
Figure 8:
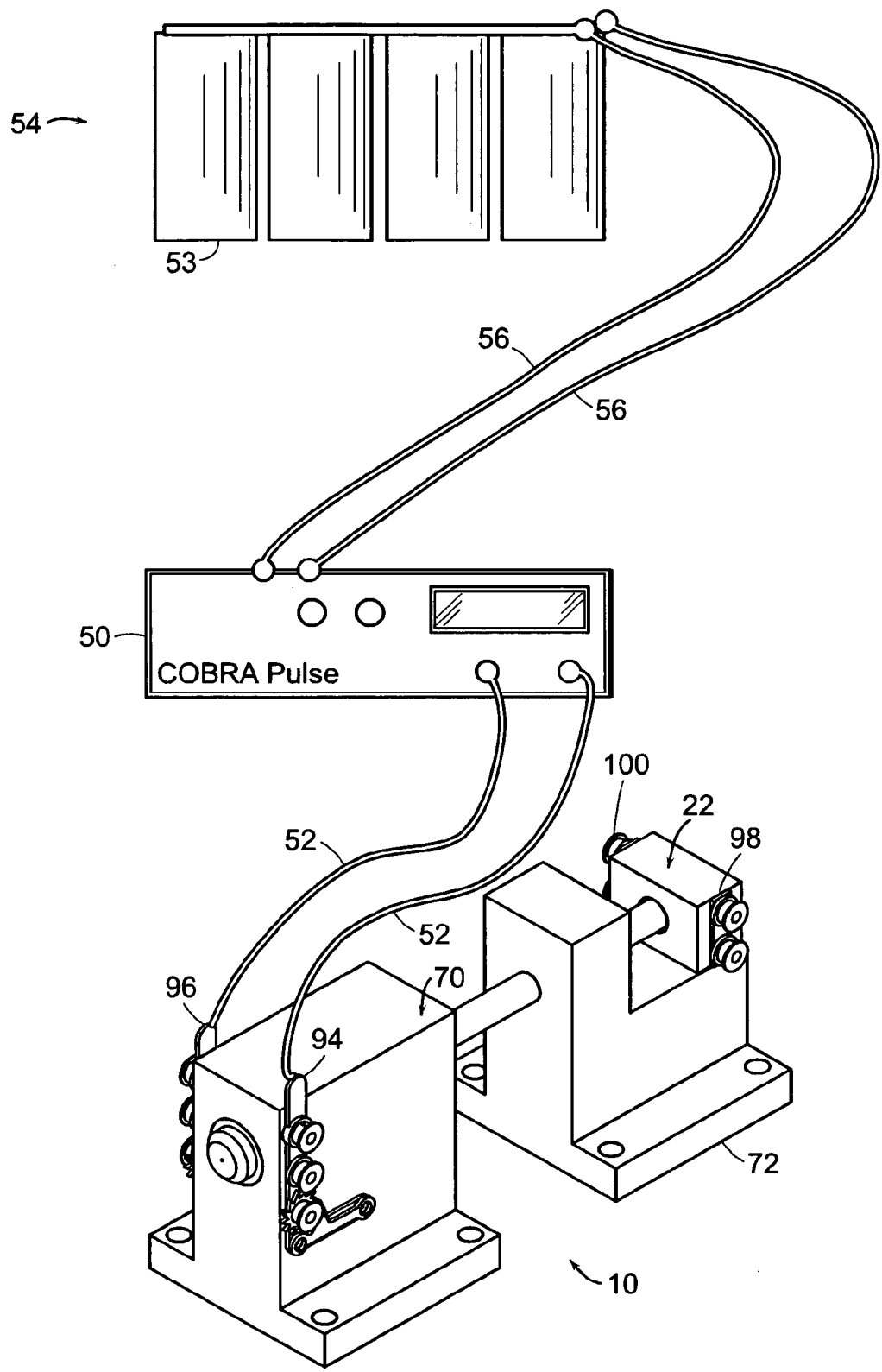
FIG. 8 is a perspective view of the drug delivery device of FIG. 6A with a controller and energy source.

In one implementation, the device 10 of FIG. 6A is connected to the controller 50 with the pair of leads 52, and the controller in turn in connected to the capacitor bank 54 with another pair of leads 56, as illustrated in FIG. 8. As mentioned above, the capacitors of the bank 54 are energized through a power source in the controller 50 or by an external power source. Once energized, the capacitors, under the direction of the controller 50, discharge to apply a potential across the wires 30 via the conductive bars 94 and 96 through the leads 52. The wires 30 heat up and contract such that the piston 18 is pushed towards the orifice 14, thereby forcing the drug D from the chamber 12 of the vial 80 out the orifice 14.

Although shown as blocks, the base portions 70 and 72 can have any suitable geometry which facilitates the use of the device 10 of FIG. 6A in a particular application. As mentioned before, the device can be mounted within an applicator that is held by an operator.

Figure 9A:
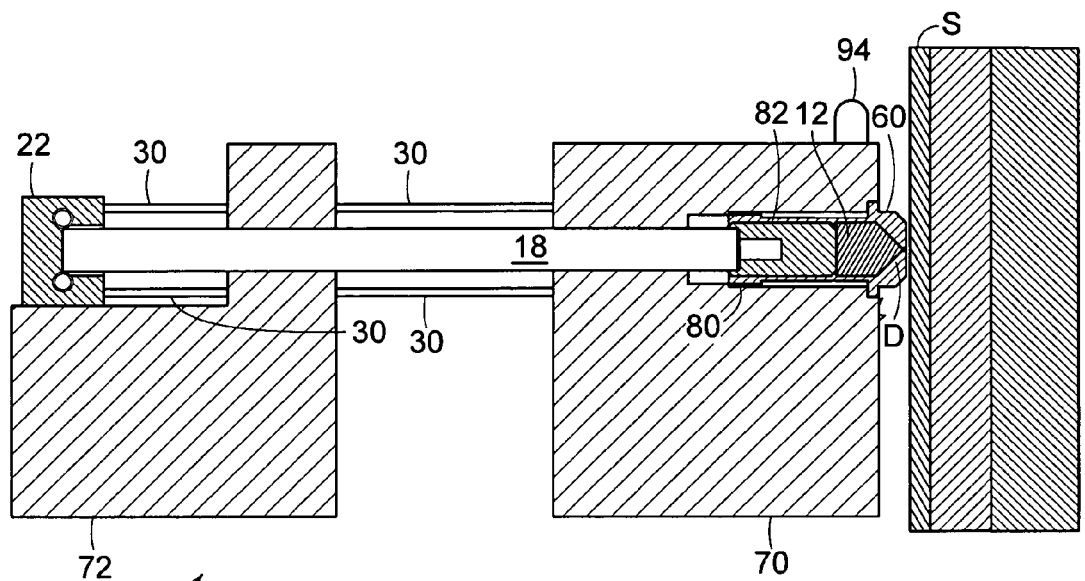
FIG. 9A is a cross-sectional view of the drug delivery device taken along the line 9A-9A of FIG. 6D prior to delivery of a drug.
Figure 9B:
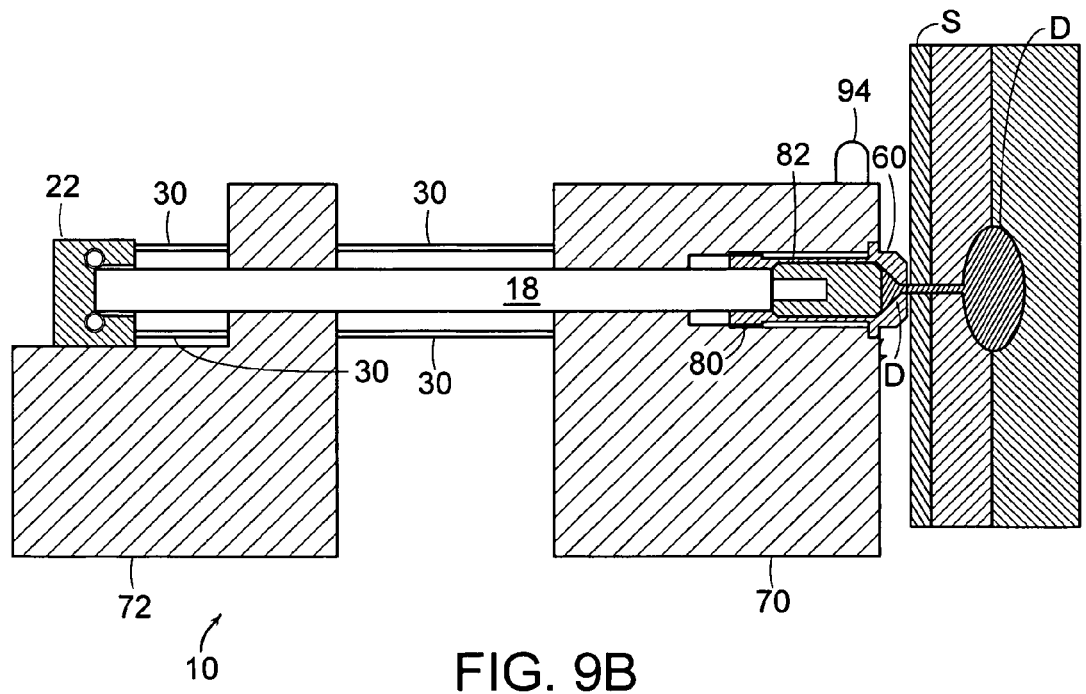
FIG. 9B is a cross-sectional view of the drug delivery device during drug delivery.

Referring to FIGS. 9A and 9B, as well as to FIG. 6A, to use the device 10, the operator positions the applicator such that a surface 101 of the vial 80 is placed against the skin, S, of the body. Prior to the placement of the surface 101 against the skin, or while the surface 101 is positioned against the skin, the capacitor bank 54 is energized, as described earlier. The operator then triggers the device 10 through the controller 50 to discharge the capacitor bank 54, thereby applying a potential across the wires 30 which causes them to contract. As the wires 30 contract, they pull the push block 22 which pushes the piston 18, which in turn pushes the plunger 82 towards the orifice 14 to force the drug, D, from the chamber 12 through the orifice 14 into the body. After the energy in the capacitor bank is depleted, the potential across the wires 30 is removed which causes the wires 30 to extend to their original length as the coiled spring 37 pushes the push block 22 away from the vial 80. The chamber 12 can then be refilled if desired with additional drug to be injected into another body.

The device 10 of FIG. 1A or 5A can be used as a single-use device or for multiple uses. When used as a multiuse device, the cycle time between uses can be 0.5 seconds or less.

Figure 10:
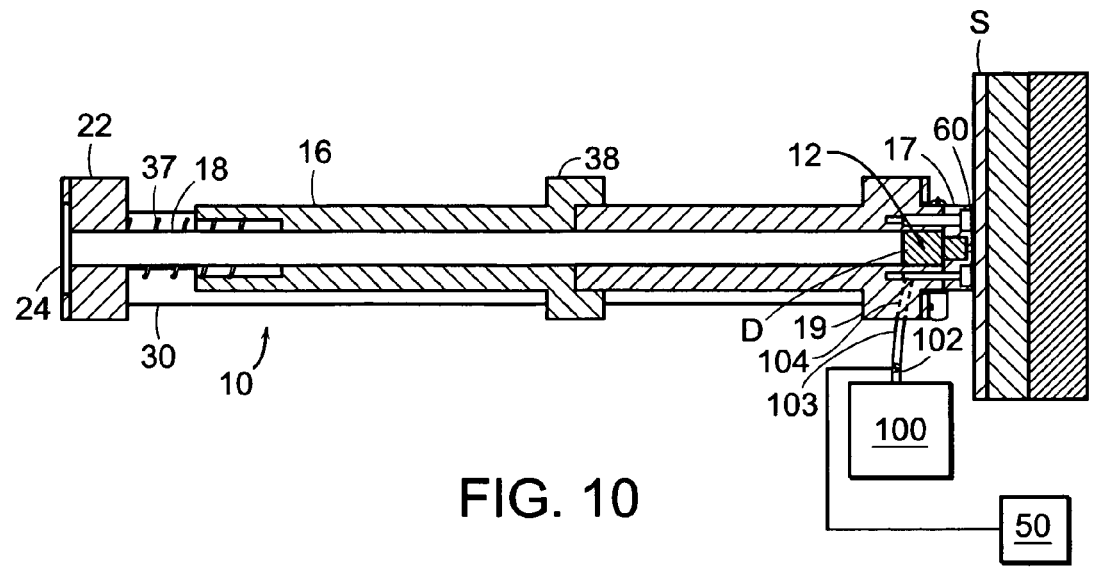
FIG. 10 is cross-sectional view of another alternative embodiment of the drug delivery device in accordance with the invention.

For example, there is shown in FIG. 10 the device 10 of FIG. 1A coupled to a reservoir 100 that supplies the chamber 12 with a sufficient amount of drug, D, for each injection, and holds enough drug for approximately 20 to 200 or more injections. Alternatively, individual doses may be provided in a plurality of reservoirs sequentially coupled to the delivery device 10. A valve 102 is associated with a tube 103 connecting the reservoir 100 with an inlet port 104 of the chamber 12. The valve 102 is opened and closed under the direction of the controller 50, or an additional controller, to allow the desired amount of drug into the chamber 12 for each injection. The device 10 of FIG. 6A can also be coupled to a similar reservoir that is operated in the manner just described.

When the device 10 of FIG. 10 is in use, the controller 50 instructs the valve 102 to open to allow the drug to flow from the reservoir 100 through the inlet port 104 into the chamber 12, and, after a prescribed period of time, the controller 50 directs the valve 102 to close so that a desired amount of the drug is held in the chamber 12 for a single injection.

Next, or while the chamber 12 is being filled with drug, the operator positions the applicator to place the surface 60 of the head 17 against the skin, S, of the body. Meanwhile, the capacitor bank 54 is energized as described above. The operator then triggers the device 10 through the controller 50 to discharge the capacitor bank 54, thereby applying a potential across the wires 30 which causes them to contract. As the wires 30 contract, they pull the push block 22 which pushes the piston 18 towards the head 17 to force the drug, D, from the chamber 12 through the orifice 14 into the body. After the energy in the capacitor bank is depleted, the potential across the wires 30 is removed which causes the wires 30 to extend to their original length as the coiled spring 37 pushes the push block 22 away from the head 17. The controller 50 then instructs the valve 102 to open to refill the chamber 12 with additional drug from the reservoir 100 to be injected into another body.

When the device 10 is intended for multiple uses, it may be desirable to provide some type of protective sterile barrier between the head 17 and the skin of the body to eliminate or at least minimize exposing a subsequent body with contaminants from a previous body.

Figure 11:
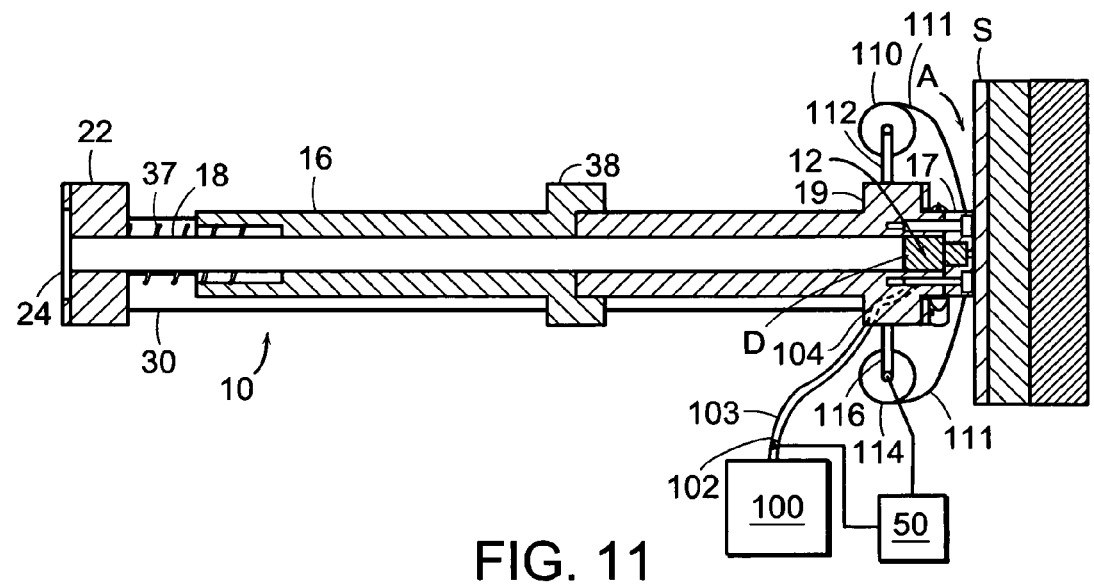
FIG. 11 illustrates the drug delivery device of FIG. 10 with a protective sterile ribbon in accordance with the invention.

For example, there is shown in FIG. 11 the device 10 provided with a supply of ribbon from a supply roller 110 mounted to the device 10 with a support 112. A sheet of ribbon 111 passes between the face 60 (see, e.g., FIG. 1A) and the skin, S, of the body. After use, the ribbon 111 is spooled onto a take-up roller 114 that is mounted to the device 10 with a support 116. The ribbon 111 is wide enough to cover the face 60 such that none of the face 60 makes contact with the skin, S. The ribbon 111 is made of any suitable material that prevents cross-contamination between biological bodies, such as a non-porous flexible material.

The operation of the take-up roller 114, and, optionally, the supply roller 110, can be controlled by the controller 50, or an additional controller. Thus, when in use, the device 10 ejects drug from the orifice 14 through the ribbon 111 into the body. After the drug has been injected into the body, additional drug can be supplied from the reservoir 100 according to the techniques described above, while the controller 50 instructs the roller 114 to take up a sufficient amount of ribbon 111 in the direction A, so that the next body is exposed only to a new sterile portion of the ribbon 111 during the injection procedure.

In other implementations, a new sterile head 17 is positioned on the device 10 after an injection, while the previous head 17 is disposed in a suitable manner.

Figures 12A, 12B:
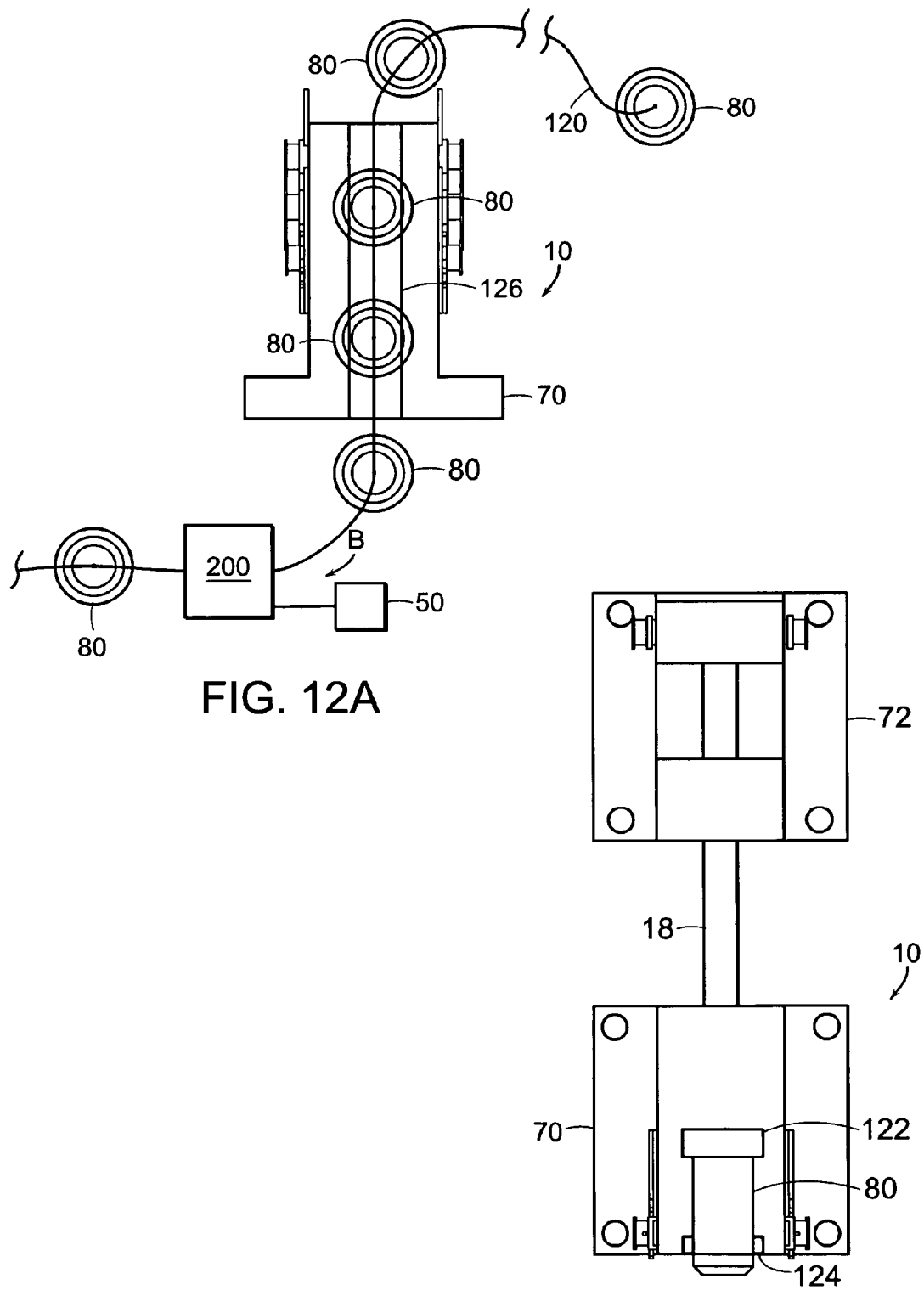
FIGS. 12A and 12B illustrate yet another alternative embodiment of the drug delivery device in accordance with the invention.

Referring now to FIGS. 12A and 12B, there is shown another embodiment of the device 10 suitable for multiuse operations. The device 10 is provided with a series of vials 80 connected together, for example, with a flexible web 120. Enlarged regions 122 and 124 (see, e.g., FIG. 7A) of the vials 80 engage with a slot 126 of the base portion 70. Thus, after each injection, a driver 200, separate from or integral with the device 10, pulls the web 120, and hence the vials 80, in the direction B until a vial filled with drug and fed from the top of the base 70 is suitably coupled with the piston 18 for the next injection. The injection procedure proceeds as described earlier, for example, for the embodiment of FIG. 6A. As such, the device 10 can be used in a "machine-gun" like manner, with new vials being fed through the top of the base 70, while depleted vials are pulled out from the bottom of the base 70. The driver 200 can be under the control of the controller 50 or another controller. The vials 80 could be fed and removed from the side of the base portion 70. Moreover, such an automated arrangement could be implemented with the device 10 of FIGS. 1-4.

In some implementations, the controller 50 is coupled with a sensor that detects skin properties. This information can be used to servo-control the actuator 28 to tailor the injection pressure, and, therefore, the depth of penetration of drug into the skin for a particular application. For instance, when the device 10 is used on a baby, the sensor detects the softness of the baby's skin, and the controller 50 uses the properties of the baby's skin and consequently reduces the injection pressure. The injection pressure can be adjusted, for example, by controlling the current amplitude applied to the wires 30 and/or the current pulse rise time and/or duration. When used on an adult or someone with sun damaged skin, the controller may increase the injection pressure. The injection pressure may be adjusted depending on location of the skin on the body, for example, the face versus the arm of the patient. The injection pressure can also be tailored to deliver the drug just underneath the skin or deep into muscle tissue. Moreover, the injection pressure may be varied over time. For instance, in some implementations, a large injection pressure is initially used to pierce the skin with the drug, and then a lower injection pressure is used to deliver the drug. A larger injection may also be used to break a seal that seals the chamber or vial.

Skin is a non-linear, viscoelastic material. Microscopic changes in cellular mechanical properties or adhesion between tissue can be observed as macroscopic changes in static or dynamic mechanical tissue properties. These factors combine to determine the behavior of skin in response to outside stimulants. For small force perturbations about an applied static force, the skin mechanical dynamics can be approximated as a linear mechanical system relating the applied force F(t) to skin deformation x(t) as:

$$F(t) = I\frac{d^2 x(t)}{dt^2} + B\frac{dx(t)}{dt} + Kx(t), \quad (1)$$

where I is the inertia in kg, B is the viscosity in kg/s, and K is the stiffness in N/m of skin. After taking the Laplace transform of equation (1), the equivalent transfer function representing the mechanical compliance of the skin as a function of frequency, ω, is:

$$\frac{x(\omega)}{F(\omega)} = \frac{G\omega_n^2}{\omega^2 + 2\varsigma\omega_n\omega + \omega_n^2}, \quad (2)$$

where (3)

$$G = \frac{1}{K},$$

$$\omega_n = \sqrt{\frac{K}{I}}, \quad (4)$$

and (5)

$$\varsigma = \frac{1}{2}\frac{B}{\sqrt{IK}}.$$

A Bode plot (gain vs. freq.) can be obtained for the above mechanical system, illustrating a decrease in compliance with increase skin stiffness. A tailored stochastic sequence can also be performed by tuning F(t) to pull out the relevant parameters. As such, skin properties can be determined with system identification techniques. Such techniques are described in the article "The Identification of Nonlinear Biological Systems: Volterra Kernel Approaches," by Michael J. Korenberg and Ian W. Hunter, Annals of Biomedical Engineering, Vol. 24, pp. 250-269, 1996, the entire contents of which are incorporated herein by reference.

Figure 13:
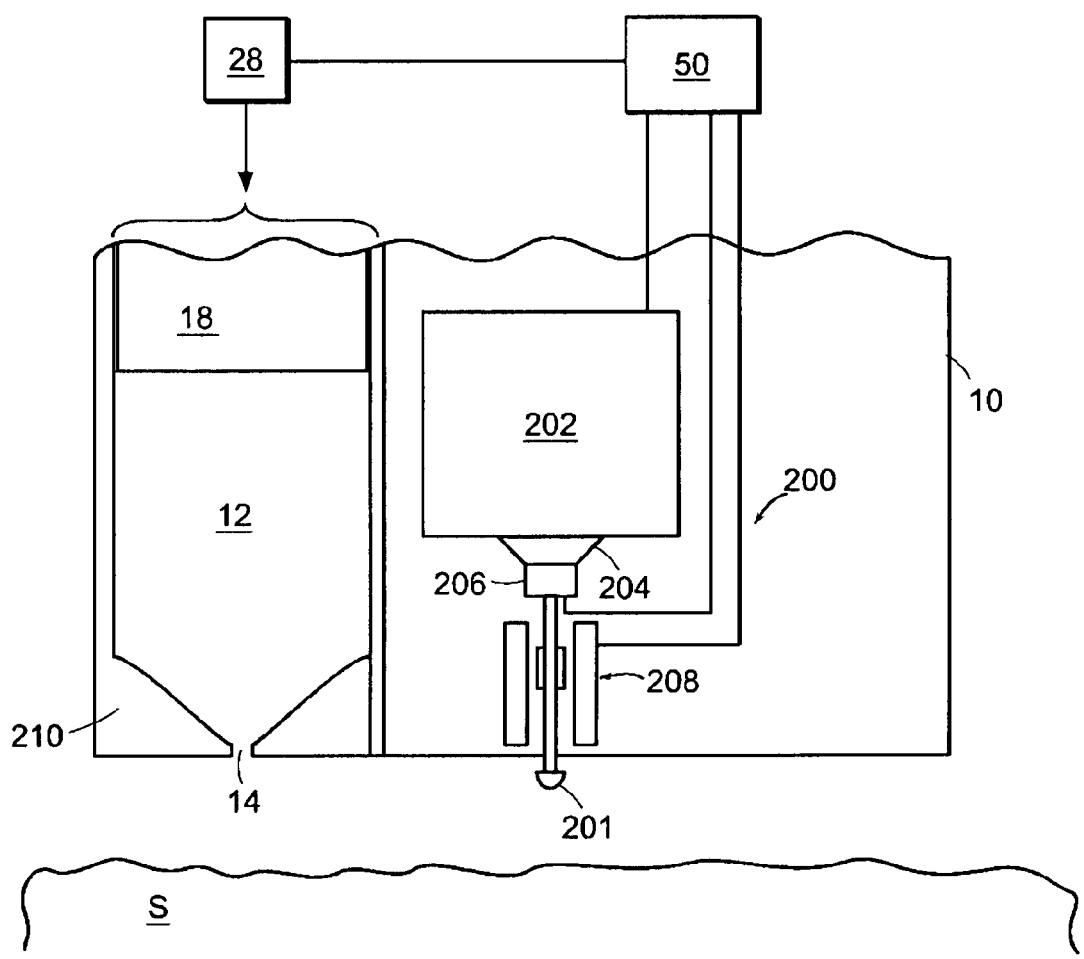
FIG. 13 illustrates the drug delivery device with a sensor used to detect properties of the skin in accordance with the invention.

Referring now to FIG. 13, there is shown a skin property sensor 200 associated with the drug delivery device 10. The sensor 200 includes an electromagnetically driven voice coil 202 coupled to a force transducer 206 with a flexure 204. The force transducer 206 in turn is coupled to a linear variable differential transducer (LVDT) 208 with a sensor tip 201. In the implementation shown, the voice coil 202, the force transducer 206, and the LVDT 208 are connected to a controller such as the controller 50, which drives the sensor 200 as well as receives signals from the sensor 200. The sensor 200 can be integrated with the device 10, or it can be a separate unit. As shown, the sensor is positioned within the device 10, with the sensor tip 201 located near the orifice 14 (see also FIGS. 1A, 5A, and 6A).

Accordingly, when the device 10 is used with the sensor 200, the device 10 is initially placed against the skin, S, of the body such that the sensor tip 201 also rests against the skin. The controller 50 then drives the voice coil 202, for example, up to 20 kHz, to perturb the skin, while the force transducer 202 detects the force the tip 201 applies to the skin, and the LVDT 208 detects the displacement of the skin. This data is fed back to the controller 50 which then evaluates the skin properties with the system identification techniques described earlier. Based on the detected skin properties, the controller 50 directs the actuator 28 to eject the drug, D, contained in the chamber 12, through the orifice 14 with the desired injection pressure. Alternatively, a body portion 210 in which the chamber 12 is defined can function as the sensor tip 201. In such implementations, the body portion 210 would be coupled to the LVDT 208 and force sensor 206 so that the chamber 12, body portion 210, and sensor 200 would be positioned in line.

Figure 14:
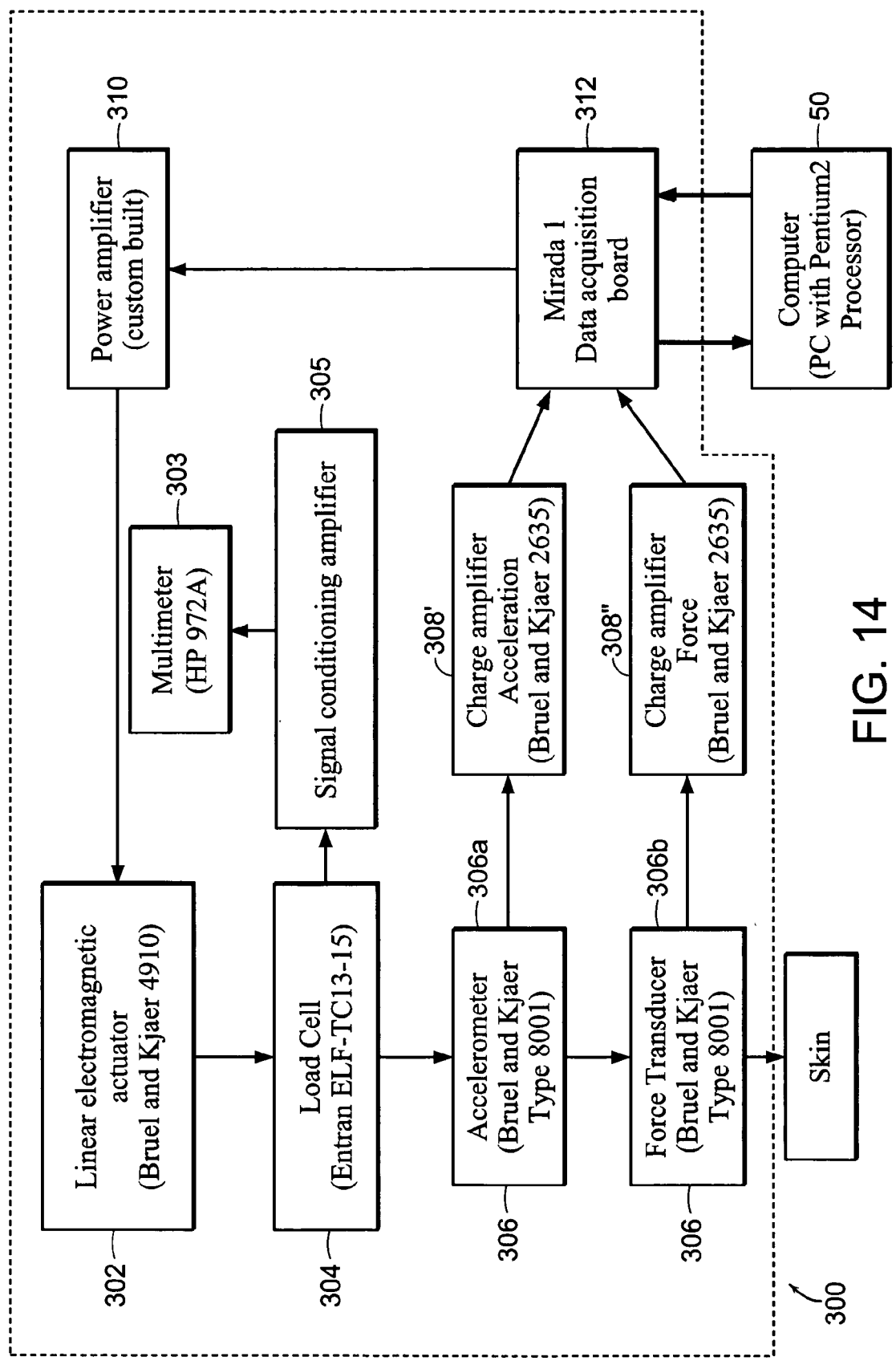
FIG. 14 is a block diagram of an alternative embodiment of the sensor used to detect properties of the skin in accordance with the invention.

Other skin property sensor arrangements can also be used with the device 10, such as the sensor configuration 300 shown as a block diagram in FIG. 14. The sensor 300 includes a linear electromagnetic actuator 302 (e.g., model no. 4910, available from Bruel and Kjaer) vertically mounted to a rigid frame. A strain gauge type load cell 304 (e.g., model no. ELF-TC13-15, available from Entran, of Fairfield, N.J.) is mounted to the actuator platform for the purpose of measuring the DC offset of the system corresponding to the static loading, as measured with a multimeter 303 (e.g., model no. HP 972A, available from Hewlett Packard, or Palo Alto, Calif.) via a signal conditioning amplifier 305. Below the load cell 304 is an impedance head 306 (Bruel and Kjaer model no. 8001) consisting of a piezoelectric accelerometer 306a and a piezoelectric force transducer 306b. The two outputs from the accelerometer record the force applied to the skin and its resulting acceleration. Two charge amplifiers 308', 308'' (generally 308) (Bruel and Kjaer model no. 2635) transform the force to a proportional voltage and doubly integrate the acceleration to give the skin displacement. The actuator 302 is driven by an algorithm, such as a Visual BASIC program, that simulates a Dynamic Signal Analyzer through a power amplifier 310. The algorithm outputs a swept sinusoidal signal within a range of pre-determined frequencies. This modulation is a small perturbation on top of an initial static load, which is determined from the output voltage of the load cell 304. The measured force and displacement of the actuator are then input to two separate channels of a data acquisition board 312 and used to calculate the compliance transfer function gain and phase with a computer or the controller 50. In one implementation, there is a 50 kHz per channel of the data acquisition board, which can be increased to 100 kHz per channel when multiplexed. The A/D is 18 bits with ±4.5 V, while the D/A is 18 bits with ±3.0 V. Like that shown in FIG. 13 for the sensor 200, the sensor 300 is preferably associated with the device 10 through the controller 50. Accordingly, properties of the skin are analyzed by the controller 50 based on the data from the sensor 300. The controller 50 then directs the device 10 to eject drug into the body with the appropriate injection pressure.

Although the sensors 200 and 300 are shown in combination with the device 10, the sensors can be combined with other types of medical devices. For example, the sensor can be combined with other types of needleless injectors such as those using magnetic, chemical, hydraulic, and spring actuators, and those described in U.S. application Ser. No. 10/200,574 filed Jul. 19, 2002, and U.S. Provisional Application No. 60/409,090 filed Sep. 6, 2002, incorporated by reference in their entireties. Additionally, the sensor can be combined with injectors that use needles, such as microneedle injectors, and those described in U.S. application Ser. No. 10/238,844 filed Sep. 9, 2002 and Ser. No. 10/278,049 filed Oct. 21, 2002, also incorporated by reference in their entireties. Advantageously, the sensed properties can be used to control the depth and/or insertion force of the needles.

Furthermore, the sensors 200, 300 can be used to measure skin properties of a subject, as described above, or they can be used, to measure properties of other body surfaces. For example, the sensor can be used to measure properties of the internal anatomy of subject, such as the surface of an internal cavity or organ during a surgical procedure.

In some embodiments, the sensors 200 and 300 can be configured as stand alone units. Thus, the system components discussed in relation to FIGS. 13 and 14 can be packaged within a single housing. The housing can be tethered to an external power source, or can include an internal power source, such as a battery. Additionally, a stand alone unit can be configured as a wearable device that can attach to a patient's body using a bandage, or an adhesive. For example, a small force transducer and an accelerometer can be packaged in an adhesive bandage that is placed on the skin. The transducer first resonates at a resonant frequency (e.g., 50 Hz) for a period of time (e.g., several seconds). The transducer stimulates the local skin and the accelerometer detects the displacement of the skin. A controller can then record the resulting skin displacement in a memory and calculate the compliance gain of the skin. The controller can further determine the mechanical behavior of the skin (e.g., stiffness) using the calculated compliance gain. Still further, the controller can further identify the type of skin using its calculated mechanical behavior and/or compliance gain (e.g., that of a baby or of an adult). The sensor can ultimately generate a signal or command used as an indicator to an operator and/or a control signal to a medical device.

While this invention has been particularly shown and described with references to preferred embodiments thereof, it will be understood by those skilled in the art that various changes in form and details may be made therein without departing from the scope of the invention encompassed by the appended claims. For example, contractile polymers, or any other suitable contracting material, can be used instead of the shape memory alloy. The device 10 may include multiple chambers or may accommodate multiple drug vials. Thus, the device 10 is able to deliver drug sequentially or simultaneously. For example, the device 10 is able to deliver two or more drugs at once to the body.

What is claimed is:

1. A method for injecting drug into a biological body comprising:
   holding a drug to be delivered to the body in a drug injector;
   measuring displacement of the skin with applied force;
   prior to any injection, adjusting the injection pressure of the drug injector with a servo-controller based on the displacement; and
   injecting the drug into the body.

2. The method of claim 1 further comprising a controller which drives a source probe that stimulates a local surface of the outer layer of the skin, the controller being coupled to a detector, and the controller driving the source probe using a stochastic sequence and determining a property of the outer layer using a measured displacement received from the detector.

3. The method of claim 2, wherein the measured property is indicative of compliance.

* * * * *